United States Patent [19]

Jones et al.

[11] 4,442,697

[45] Apr. 17, 1984

[54] PRE-STRESSED IMPACT TESTING DEVICE

[75] Inventors: Brian L. Jones; David L. Johnson; Merlin H. Moseman, all of Omaha, Nebr.

[73] Assignee: InterNorth, Inc., Omaha, Nebr.

[21] Appl. No.: 359,742

[22] Filed: Mar. 19, 1982

[51] Int. Cl.³ .............................................. G01N 3/30
[52] U.S. Cl. .......................................... 73/12; 73/794
[58] Field of Search ............................. 73/12, 794, 844

[56] References Cited

U.S. PATENT DOCUMENTS

| | | | |
|---|---|---|---|
| 2,699,672 | 1/1955 | Couch et al. | 73/838 X |
| 3,157,046 | 11/1964 | Orner | 73/12 X |
| 3,218,847 | 11/1965 | Starer et al. | 73/12 X |
| 3,590,631 | 7/1971 | Gonze | 73/844 X |

FOREIGN PATENT DOCUMENTS

800808  1/1981  U.S.S.R. ................................ 73/12

*Primary Examiner*—S. Clement Swisher
*Assistant Examiner*—Brian R. Tumm
*Attorney, Agent, or Firm*—Zarley, McKee, Thomte, Voorhees & Sease

[57] ABSTRACT

A pre-stressed impact testing device designed to measure the energy which is absorbed during fracture of metal samples under pre-stressed conditions. The device includes a base portion and a pendulum supporting portion which is positioned thereabove. The base portion includes first and second elongated and horizontally spaced-apart beams having opposite ends with a third beam secured to and extending between the first and second beams at one end thereof. A hydraulic ram is secured to and extends between the other ends of the first and second beams for selectively moving the other ends of the first and second beams away from each other so that the first and second beams will be elastically stressed. Connectors are provided on each of the first and second beams for attachment to the opposite ends of the sample material whereby the sample material will be placed in stress when the first and second beams are elastically stressed. A pendulum is positioned on the pendulum supporting portion for impacting and fracturing the sample material. A recorder is provided for measuring the amount of travel of the pendulum after it fractures the sample material.

11 Claims, 5 Drawing Figures

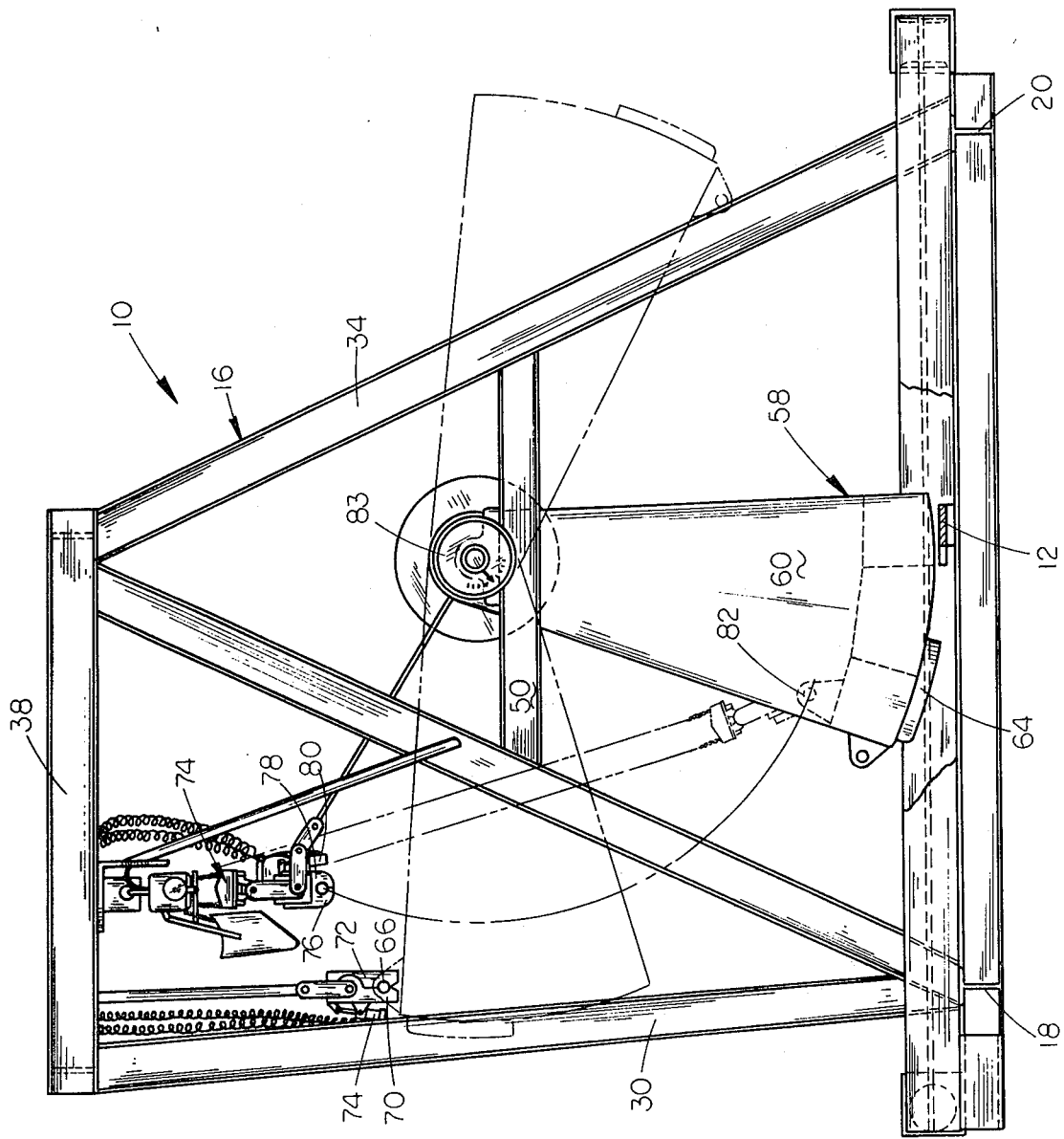

PRE-STRESSED IMPACT TESTING DEVICE

BACKGROUND OF THE INVENTION

This invention relates to an impact testing device and more particularly to an impact testing device wherein the sample material to be tested is in a stressed condition.

In the design of pipelines, it is necessary to determine the resistance of the pipeline steel to cracking and bursting. Since the pipeline in its operational condition will be under stress from whatever it is carrying, any testing of the pipe for cracking and bursting should ideally be done with the pipeline under stress. Ordinarily, such testing is done through a burst test procedure which requires pressurizing a one thousand foot section of actual pipe with a small charge being detonated to force a crack. A burst test destroys a lot of expensive pipe and can very easily result in an expenditure of approximately $750,000 for each burst test. Impact testing equipment such as the Charpy or Battelle drop-weight tear test machines were designed to measure the energy absorbed during the fracture of free-standing unstressed samples. The Charpy and Battelle machines were designed to eliminate the need for the expensive burst tests but the Charpy and Battelle machines are unable to simulate actual conditions since the material being tested is unstressed.

Therefore, it is a principal object of the invention to provide an impact testing device wherein the material to be tested is pre-stressed.

Another object of the invention is to provide a pre-stressed impact testing device including means to insure that the sample will be extended during impact fracture to eliminate loss of the pre-stressed load.

A further object of the invention is to provide an impact testing device which simulates actual operational conditions.

A further object of the invention is to provide an impact testing device which enables the determination of the energy absorbed during fracture of metal samples under pre-stressed conditions which simulate actual operational experience.

These and other objects will be apparent to those skilled in the art.

BRIEF DESCRIPTION OF THE DRAWINGS

FIG. 2 is a side elevational view of the device with the broken lines indicating the movement of the pendulum;

SUMMARY OF THE INVENTION

Figure 1:
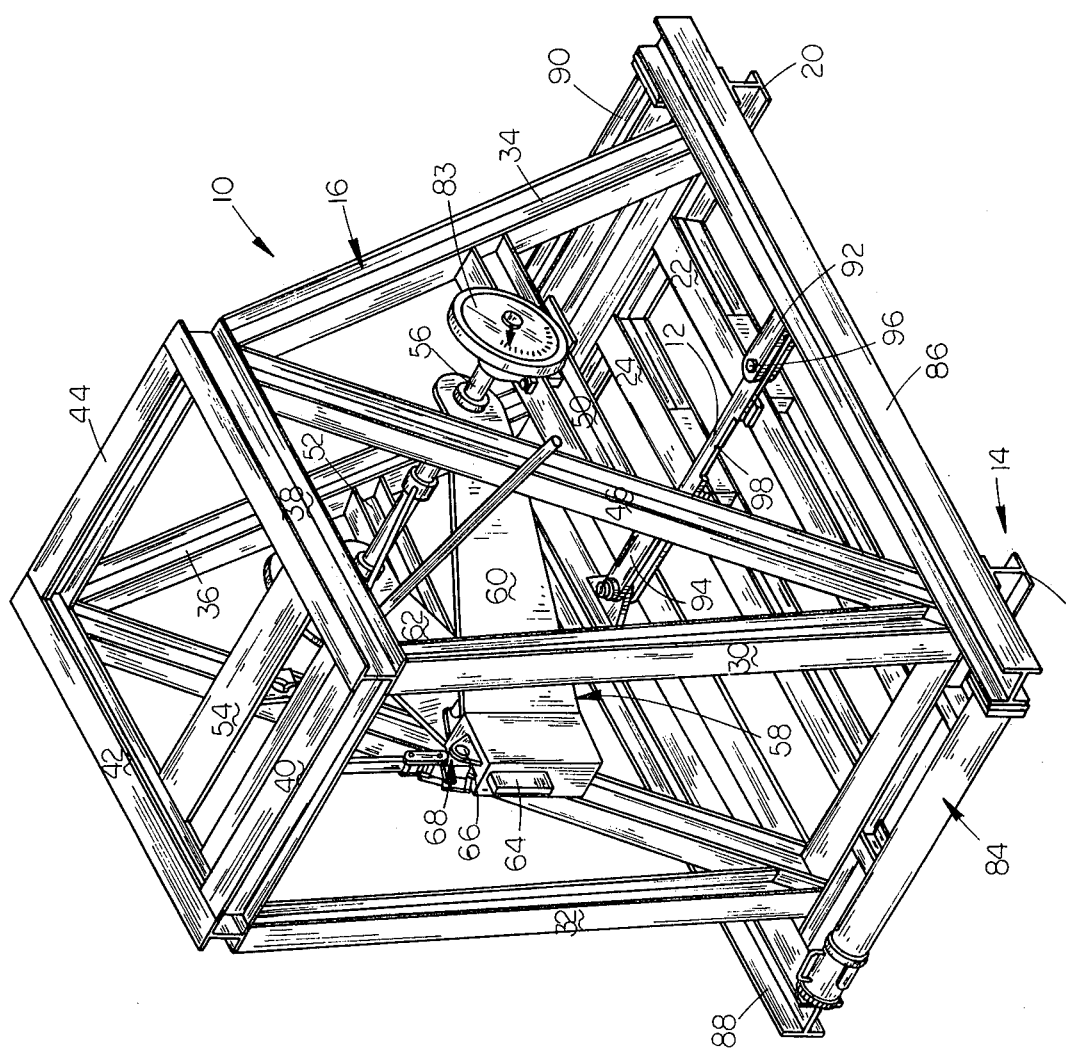
FIG. 1 is a perspective view of the impact testing device.
Figure 4:
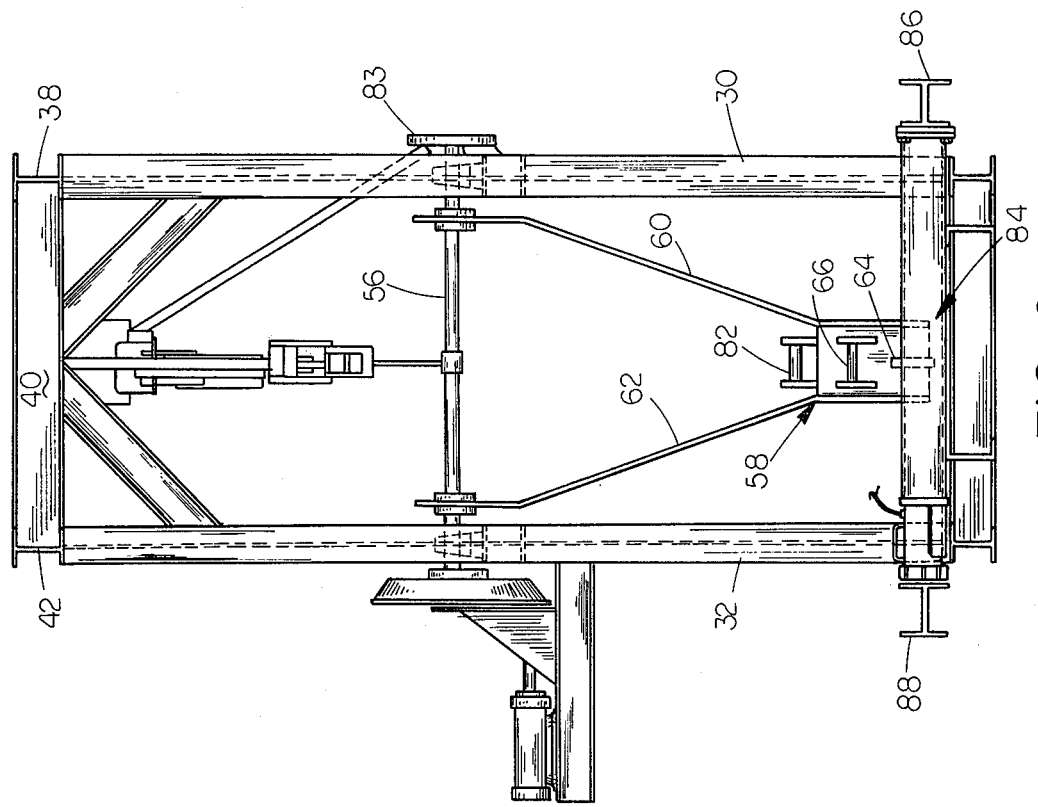
FIG. 4 is an end elevational view of the device.
Figure 3:
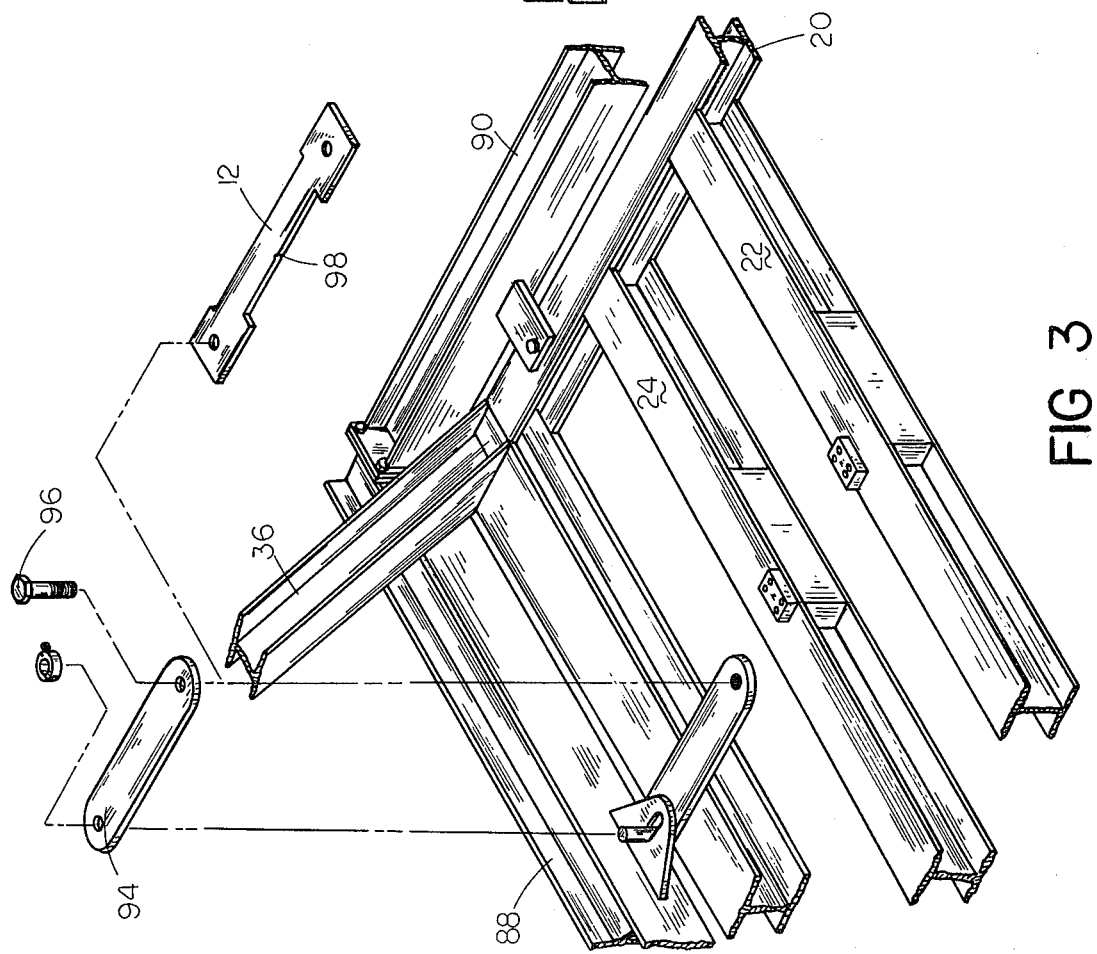
FIG. 3 is a partial exploded perspective view of the invention.
Figure 5:
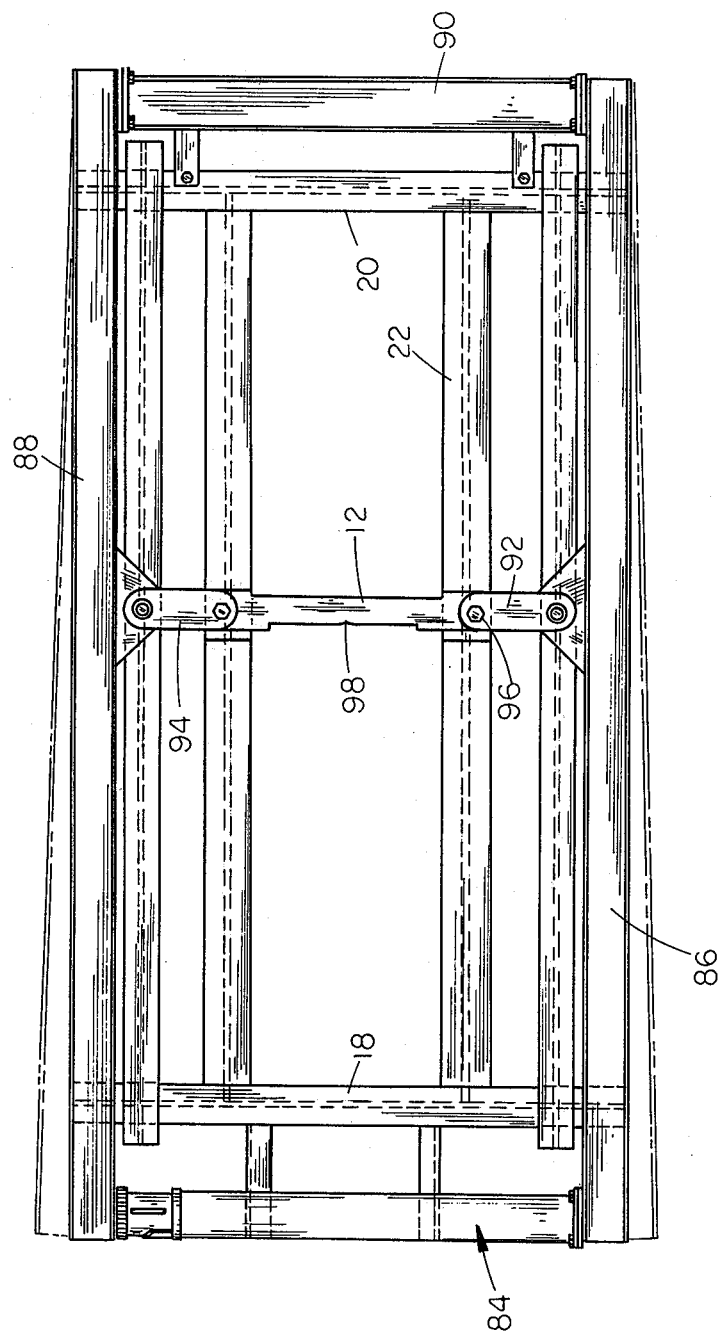
FIG. 5 is a top elevational view of the lower portion of the device.

The impact testing device of this invention comprises a frame means having a base portion with a pendulum supporting portion positioned thereabove. The base portion includes first and second beams or frame members having a third beam or frame member secured to and extending between the first and second beams at one end thereof. A hydraulic ram is secured to and extends between the other ends of the first and second beams and is designed to selectively move the other ends of the first and second beams away from each other so that the first and second beams may be elastically stressed during the testing of the test material. Connector means are provided on each of the first and second frame members between the ends thereof so that the test material may be suspended therebetween and so that the sample or test material will be placed in stress when the first and second beams are elastically stressed. A pendulum means is mounted on the pendulum supporting portion for impacting and fracturing the sample material. A winch mechanism is provided on the pendulum supporting portion for maintaining the pendulum means in its ready position. When the winch means is released, the pendulum means swings downwardly and impacts the stressed test material and fractures the same. Means is provided so that the amount of travel of the pendulum, after it fractures the sample material, may be determined. By measuring how much the sample material prevents the pendulum from swinging through a 180° arc, it is possible to calculate the energy required to split the test material.

DESCRIPTION OF THE PREFERRED EMBODIMENT

The impact testing machine of this invention is referred to generally by the reference numeral 10 and is designed to measure the energy absorbed during fracture of a metal sample which is referred to generally by the reference numeral 12. Machine 10 is generally comprised of base portion 14 and pendulum supporting portion 16 positioned thereabove.

Base portion 14 generally comprises a pair of frame members 18 and 20 which are preferably secured to a suitable supporting surface such as a concrete floor or the like by any convenient means. Frame members 22 and 24 are secured to and extend between the frame members 18 and 20 as best seen in FIG. 1.

Pendulum supporting portion 16 includes upstanding frame members 30, 32, 34 and 46 which are secured to frame members 18 and 20 and which extend upwardly therefrom. Frame members 38, 40, 42, and 44 are secured to the upper ends of the frame members 30, 32, 34 and 36 as illustrated in FIG. 1. Pendulum, supporting portion 16 is also provided with diagonally extending braces or frame members 46 and 48. Frame member 50 is secured to and extends between frame members 46 and 34 while frame member 52 is secured to and extends between frame members 48 and 37. Frame member 54 is secured and extends between frame members 38 and 42 as best illustrated in FIG. 1.

Shaft 56 has its opposite end rotatably mounted in bearings positioned on frame members 50 and 52. A V-shaped pendulum 58 has its legs 60 and 62 secured to shaft 56 for rotation therewith. Strike plate 64 is mounted on the end of the pendulum 58 and is designed to strike the sample 12 as will be described in more detail hereinafter. Pendulum 58 is provided with a shaft or pin 66 which is adapted to be received by the locking device 68 which extends downwardly from the upper portion of the pendulum supporting portion 16 as seen in FIG. 1. Locking device 68 includes a pair of jaw members 70 and 72 which are pivotally movable towards each other so as to strap the pin 66 to maintain the pendulum in the "ready" position illustrated in FIG. 1.

The numeral 74 refers to a winch and locking assembly which is detachably connected to the pendulum 58 so that the pendulum may be moved from the position illustrated by solid lines in FIG. 2 to the ready position. Assembly 74 includes a pair of movable jaw members 78 controlled by a suitable solenoid or hydraulic cylinder 80 so that the jaw members 78 and 76 may detachably grasp pin 82 on the pendulum. The numeral 83 refers to a measuring device which may be of any suitable construction but which is operatively connected to the end of a shaft 56 so that the amount of travel of the pendulum, after it strikes the sample 12, may be determined so that computation may be made of the energy required to fracture the sample.

A hydraulic ram 84 is secured and extends between the ends of beams 86 and 88 which are positioned on the frame members 18 and 20 as best illustrated in FIG. 1. Beam 90 is rigidly secured to and extends between the ends of the beams 86 and 88. Connectors 92 and 94 are secured to the beams 86 and 88 respectively and extend inwardly therefrom and are designed to be secured to the ends of the sample 12 by means of bolts or pins 96 which extend through suitable openings formed in the opposite ends of the sample 12. Extension of the hydraulic ram 84 causes the beams 86 and 88 to be deflected outwardly from each other so that the sample 12 is placed on a pre-stressed condition.

The normal method of operating the machine of this invention is as follows. If the steel in a pipeline is to be tested, a portion of the pipe is flattened and a notch 98 is formed therein by suitable means in order to initiate a small crack. The crack may be initiated by a separate bending operation, by a suitable low-energy impact in the machine herein described or otherwise as desired by the test procedure. Hydraulic ram 84 is extended to elastically bend the beams 86 and 88 outwardly from each other which causes the sample 12 to be placed in a stressed condition. Suitable pressure gauges or the like would be operatively connected to the hydraulic ram 84 so that the amount of force applied to the beams 86 and 88 may be ascertained. The winch and locking assembly 74 is connected to the pin 76 and the winch assembly is operated so that the pendulum 58 is moved from its rest position such as illustrated by solid lines in FIG. 2 to the read position illustrated in FIG. 1. When the pendulum 58 is in the ready position, the locking device 68 also locks onto the pin 66 which serves as a backup or safety to the winch and locking assembly 74. Thus, if jaw members 76 and 78 should inadvertently disengage from pin 82, the locking device 68 will prevent the pendulum from swinging downwardly.

When it is desired to fracture the sample 12, both the locking device 68 and locking assembly 74 are released which causes the pendulum to swing downwardly from the ready position. As the pendulum 58 swings downwardly, the strike plate 64 strikes the pre-stressed sample 12 and fractures the same. The pendulum continues upwardly past the position of the sample and it is the angle through which the pendulum travels after it fractures the sample that is recorded. If the sample 12 offers very little resistance to the pendulum, the amount of travel of the pendulum beyond the sample will be greater than that if the sample 12 offered greater resistance. By metering the amount that the sample 12 prevents the pendulum from swinging through a 180° arc, it is then possible to calculate the energy needed to split the sample or pipe.

The most important feature of the device is that the hydraulic ram 84 provides the requisite stress on the sample to be tested through elastic bending of the beams 86 and 88. The elastic bending of the beams and the resultant stress placed on the sample 12 insures that the sample will be extended during the impact fracture. If the beams 86 and 88 were not elastically bent, the pre-stressed load on the sample 12 would be lost during the occurrence of the impact fracture.

Thus, it can be seen that the pre-stressed impact testing device of this invention accomplishes at least all of its stated objectives.

We claim:
1. A pre-stressed impact testing device, comprising,
a frame means comprising a base portion and a pendulum supporting portion positioned thereabove,
said base portion including first and second elongated horizontally spaced frame members having opposite ends, and a third frame member secured to and extending between said first and second frame members to one end thereof,
a ram means secured to and extending between the other ends of said first and second frame members for selectively moving the said other ends of said first and second frame members away from each other whereby said first and second frame members are elastically bent,
connector means on each of said first and second frame members intermediate the length thereof for attachment to the opposite ends of the sample material whereby said sample material will be placed in stress when said first and second frame members are elastically bent,
a pendulum means mounted on said pendulum supporting portion for impacting and fracturing the sample material,
and means for measuring the amount of travel of said pendulum means after it fractures the sample material.

2. The device of claim 1 wherein said pendulum means includes a strike plate thereon for impacting the sample material.

3. The device of claim 1 wherein said pendulum means is movable between a ready position above the sample material to an impacting position.

4. The device of claim 3 wherein means is mounted on said pendulum supporting portion for raising said pendulum means to its ready position and for selectively maintaining said pendulum means in said ready position.

5. The device of claim 4 wherein said means comprises a winch and locking apparatus.

6. The device of claim 5 wherein a safety locking device is also selectively secured to said pendulum means when said pendulum means is in its ready position.

7. The device of claim 1 wherein said pendulum means comprises a shaft horizontally rotatably mounted on said pendulum supporting portion, a V-shaped yoke secured to said shaft, and a weight means at the juncture of the legs of the V-shaped yoke, and a strike plate secured to said weight means.

8. The device of claim 7 wherein means is operatively secured to said shaft for metering the rotation and travel of said shaft.

9. A device for pre-stressing an elongated sample material and for impacting the same, comprising,
first and second elongated horizontally spaced frame members having opposite ends,
means for securing the opposite ends of the sample material to said frame members intermediate the lengths thereof, means for selectively elastically bending said frame members outwardly from each other whereby the sample material will be placed in stress, and a drop weight means mounted above and between said frame members for impacting and fracturing the sample material.

10. The device of claim 9 wherein said drop weight means comprises a pendulum, and means for measuring the amount of travel of said pendulum after it fractures the sample material.

11. The method of impact testing an elongated length of sample material having opposite ends, comprising the steps of:

connecting the ends of the sample material to a pair of spaced-apart beams substantially disposed at right angles to the longitudinal axis of the sample material, deflecting the beams to create elastic deformation in the beams so that the sample material is placed in stress, commencing the fracture of the sample material by impacting the sample material while the sample material is in stress, maintaining at least some stress in the sample material after the fracture commences through the elastic deformation of the beams, and measuring the amount of resistance, to fracture, of said sample material.

* * * * *